(12) United States Patent
Braun

(10) Patent No.: US 6,258,791 B1
(45) Date of Patent: Jul. 10, 2001

(54) COMBINATION PRODUCT FOR ENHANCED GENE DELIVERY COMPRISING A HYALURONIDASE

(75) Inventor: Serge Braun, Dorlisheim (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/424,741

(22) PCT Filed: May 29, 1998

(86) PCT No.: PCT/FR98/01084

§ 371 Date: Nov. 29, 1999

§ 102(e) Date: Nov. 29, 1999

(87) PCT Pub. No.: WO98/53853

PCT Pub. Date: Dec. 3, 1998

(30) Foreign Application Priority Data

May 29, 1997 (FR) .................................................. 97 06600

(51) Int. Cl.⁷ .................................................. A61K 48/00
(52) U.S. Cl. ............................................ 514/44; 424/93.2
(58) Field of Search ...................... 514/44, 2; 435/320.1; 424/94.1, 93.2; 536/23.1; 530/350, 300

(56) References Cited

U.S. PATENT DOCUMENTS

| | | | |
|---|---|---|---|
| 5,616,483 | * 4/1997 | Bjursell et al. | 435/198 |
| 5,858,351 | 1/1999 | Podsakoff et al. | 424/93.2 |
| 6,124,270 | 9/2000 | Haensler | 514/44 |
| 6,177,410 | 1/2001 | Holt et al. | 514/44 |

FOREIGN PATENT DOCUMENTS

| | | |
|---|---|---|
| 91 12329 | 8/1991 | (WO) . |
| 95 26718 | 10/1995 | (WO) . |
| WO 95/26718 | * 10/1995 | (WO) . |

OTHER PUBLICATIONS

Anderson, "Human gene therapy", Nature, 392(Supp.):25–30, Apr. 1998.*

Verma and Somia, "Gene therapy—promises, problems and prospects", 389:239–242, Sep. 1997.*

Batra et al., "Retroviral gene transfer is inhibited by chondroitin sulfate proteoglycans/glycosaminoglycans in malignant pleural effusions", 272(18):11736–11743, May 1997.*

Madry et al., "Efficient lipid–mediated gene transfer to articular chondrocytes", Gene Ther., 7:268–291, Feb. 2000.*

Fromes et al., "Gene delivery to the myocardium by intra-pericardial injection", Gene Ther., 6:683–688, Apr. 1999.*

Dubensky et al., "Direct transfection of viral and plasmid DNA into the liver or spleen of mice", 81:7529–7533, Dec. 1984.*

Chen et al., "Persistence in muscle of an adenoviral vector that lacks all viral genes", Proc. natl. Acad. Sci. USA, 94(5):1645–1650, Mar. 1997.*

Kochanek et al., "A new adenoviral vector: replacement of all viral coding sequences with 28 kb of DNA independently expressing both full–length dystrophin and beta–galactosidase", Proc. Natl. Acad. Sci. USA, 93:5731–5736, Jun. 1996.*

Product Description for Lipofectamine™Reagent, http://www.lifetech.com/transfection/celltypes/.

Gary J. Nabel et al., "Direct Gene Transfer with DNA–Liposome Complexes in Melanoma: Expression, Biologic Activity, and Lack of Toxicity in Humans", Proc. Natl. Acad. Sci., Medical Sciences, USA, vol. 90, pp. 11307–11311, Dec. 1993.

Joseph Zabner et al., "Adenovirus–Mediated Gene Transfer Transiently Corrects the Chloride Transport Defect in Nasal Epithelia of Patients with Cystic Fibrosis", Cell, Cell Press, USA, vol. 75, pp. 207–216, Oct. 1993.

Dubensky et al, "Direct Transfer of Viral and Plasmid DNA Into the Liver or Spleen of Mice", Proceedings of the National Academy of Sciences, USA, vol. 81, 1984, pp. 7529–7533, XP002057236.

* cited by examiner

Primary Examiner—Scott D. Priebe
Assistant Examiner—Peter Brunovskis
(74) Attorney, Agent, or Firm—Burns, Doane, Swecker & Mathis, L.L.P.

(57) ABSTRACT

The invention relates to a composition, kit and methods of using the compositions and kits. The composition comprises a compound which disorganizes or degrades the extracellular matrix of a cell and a nucleic acid of interest. The composition or kit is contemplated for use in gene transfer and gene therapy.

13 Claims, 1 Drawing Sheet

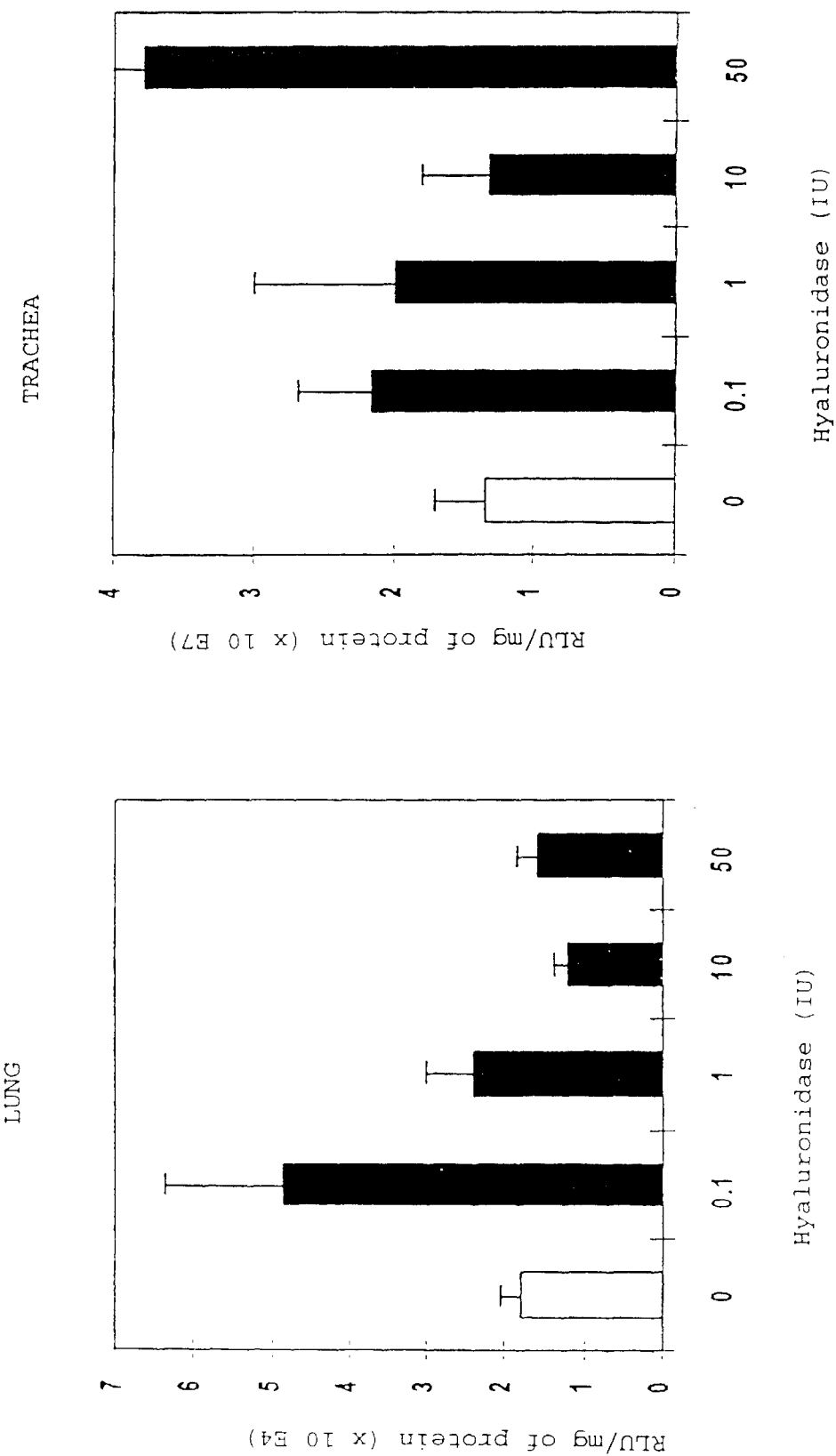

COMBINATION PRODUCT FOR ENHANCED GENE DELIVERY COMPRISING A HYALURONIDASE

The present invention relates to a product, which combines a nucleic acid and a substance which leads to disorganization of the extracellular matrix of a cell, in particular hyaluronidase, for simultaneous or consecutive use, or use which is staggered over time, with said nucleic acid being transported by an infectious viral particle or in the form of a synthetic vector. The invention also relates to the use of such a product for the purpose of promoting the transfer of the nucleic acid in question into a cell or into a host organism. The invention is of particular use in the field of gene transfer or gene therapy.

The extracellular matrix consists of protein and polysaccharide molecules which are assembled in a dense, organized network in the extracellular space of most tissues. It plays an important physiological role in maintaining the tissue architecture, and acting as a reservoir for trophic factors, chemoattractants and cell-binding factors. Hyaluronan (or hyaluronic acid) is a ubiquitous constituent of the vertebrate extracellular matrix. This linear polysaccharide, which is based on glucuronic acid and glucosamine [D-glucuronic acid 1-β-3)N-acetyl-D-glucosamine(1-b-4)], is able to exert an influence on the physicochemical characteristics of the matrices by means of its property of forming very viscous solutions. Hyaluronic acid also interacts with various receptors and binding proteins which are located on the surface of the cells. It is involved in a large number of biological processes such as fertilization, embryonic development, cell migration and differentiation, wound-healing, inflammation, tumor growth and the formation of metastases.

Hyaluronic acid is hydrolyzed by hyaluronidase. Its hydrolysis leads to disorganization of the extracellular matrix. Hyaluronidase is present in a large number of the body's biological liquids. It is produced by the acrosome of the spermatozoa and, in this situation, ensures their penetration into the ovum during fertilization. During embryogenesis, it promotes migration of the embryonic cells toward the territories which they are to colonize.

Besides its action in plasticity and tissue differentiation, the hyaluronic acid/hyaluronidase couple is also thought to be involved in certain pathological processes. Thus, this enzyme is exploited by cancer cells for extending tumors and for the angiogenesis which ensures that these tumors receive nutritional support. Hyaluronidase is cosecreted in a large number of venoms (snakes, lizards, fish, scorpions, bees, spiders, etc.) and, in this situation, is thought to increase the diffusion of these venoms in the body of the prey. Hyaluronidase is also involved in the fusogenic action of viruses such as MLV (Moloney leukemia virus) or CAEV (caprine arthritis encephalitis virus). It may also act as an agent for diffusing viruses during a bacterial contamination, as in the case of infections with herpes (Romano and Moisseiev, Metab. Pediatr. Syst. Ophtalmol. 1982, 6: 361–365).

Furthermore, hyaluronidase has been used for many years for a variety of applications in human clinical medicine: for example as an antiedema agent (Lasonil, Thiomucase), as an agent for diffusing medicines which have been injected by the intramuscular or subcutaneous route (Hyaluronidase Choay), as an anti-cancer agent, in formulating local anesthetics (Lewis-Smith, Br. J. Plast. Surg. 1986, 39: 554–558), or else as an agent for reducing myocardial lesions following an infarct. The possibility of using hyaluronidase in the field of DNA transfection has already been mentioned by Dubensky et al. (Proc. Natl. Acad. Sci. USA, 1984, 81: 7529–7533). This document demonstrates that a more uniform transfection is obtained in vivo by coinjecting plasmid DNA and a mixture of collagenase and hyaluronidase. However, the beneficial effect is not obtained with a plasmid DNA which has not previously been precipitated with calcium phosphate. Similarly, WO 95/26718 relates to a method for transferring exclusively naked DNA into cells, which method consists in using an agent which facilitates penetration of the said naked DNA into the interior of the cells. Thus, it is difficult to conceive of exploiting this technology in gene therapy using unprecipitated vectors or viral particles.

The present invention is directed towards extending the therapeutic potential of hyaluronidase to the field of gene transfer, in particular in gene therapy. It is important to have available tools which promote the distribution of gene vectors or the expression of genes within the host organism in order to improve the efficacy of this novel technology. The present invention provides an advantageous solution to this problem. The ability of hyaluronidase to promote the transfer of a nucleic acid into, or its expression in, a cell or host organism has now been demonstrated. As the examples which follow show, the intramuscular administration of a solution of hyaluronidase a few hours before injecting recombinant adenovirus into the same muscle appreciably increases expression of the recombinant gene. This combined use improves the therapeutic effect and makes it possible to employ reduced vector doses.

For this reason, the present invention relates to a combination product, which comprises at least one substance which leads to disorganization of an extracellular matrix of a host, and at least one nucleic acid of interest, for simultaneous or consecutive administration, or administration which is staggered over time, with the said nucleic acid being transported by an infectious viral particle or in the form of a synthetic vector.

The term "extracellular matrix", which is well known in the field of the art, is elaborated upon in the introductory section. Within the meaning of the present invention, "substance which leads to disorganization of the extracellular matrix" denotes any substance which acts on the integrity of the matrix, in particular exerting a total or partial degrading or destabilizing action on at least one of the constituents of the said matrix or on the bonds which unite these various constituents. While it is possible, within the context of the present invention, to have recourse to a known substance, it is also possible, if the substance is protein in nature, to have recourse to a mutant which contains one or more mutations, produced by addition, deletion and/or substitution, of one or more amino acids of the native protein, a functional fragment or else a chimeric protein which is derived from fusing sequences of varied origin. For the purposes of the present invention, the said substance can also be modified by the chemical, enzymic, etc. route with the aim of increasing its activity, its stability or else its tropism with regard to one particular cell type. The choice of a substance for use in the present invention is wide. As an indication, it can be selected from the substances which possess collagenase activity, dispase activity, trypsin activity or pronase activity.

According to one advantageous embodiment, preference is given to using a substance which is able to hydrolyze the polysaccharides which are generally present in extracellular matrices, very particularly hyaluronic acid. In this regard, a substance possessing hyaluronidase activity is very particularly suitable for implementing the invention. The hyaluronidases are described in Kreil (Protein Sci., 1995, 4: 1666–1669). The hyaluronidase can be a hyaluronidase which is derived from a mammalian, reptilian or hymenopteran hyaluronate glycanohydrolase, from a hyaluronate glycanohydrolase from the salivary gland of the leech, or from a bacterial, in particular streptococcal, pneumococcal and clostridial hyaluronate lyase. Of these, preference is very particularly given to bovine testicular hyaluronidase. Preference will be given to using a substance which exhibits a degree of homology of at least 70%, advantageously of at least 90% and, preferably, of at least 95%, with the sequence of an hyaluronidase or a functional fragment of this hyaluronidase, with the important consideration being that the hyaluronidase activity is conserved. This enzymic activity can be assessed by conventional techniques such as those described in Hynes and Ferretti (Methods Enzymol., 1994, 235: 606–616) or Bailey and Levine (J. Pharm. Biomed. Anal., 1993, 11: 285–292).

The substance which goes to make up the combination product according to the invention can be a commercially available substance, preferably a substance which is acceptable from the pharmaceutical point of view. According to another approach, it is possible to produce the substance by the recombinant route using the techniques which are conventional in this field of the art. Finally, it is also possible to conceive of introducing the sequence encoding the said substance into the nucleic acid of interest or an expression vector under the control of elements which are suitable for expressing it in a cell or a host organism. This latter can then be administered before, or at the same time as, the nucleic acid of interest. Implementing this specific embodiment is within the capability of the skilled person.

Within the context of the present invention, the nucleic acid of interest can be a sense or antisense oligonucleotide, ribonucleic acid or deoxyribonucleic acid. These designations are conventionally used in molecular biology. In brief, "sense" refers to a nucleic acid which possesses a sequence which is homologous with or identical to a target sequence, whereas antisense refers to a nucleic acid which possesses a sequence which is homologous with or identical to a sequence which is complementary to a target sequence. In conformity with the aims pursued by the present invention, the nucleic acid of interest contains at least one gene of interest and elements which enable it to be expressed in a cell or a host organism. The nucleic acid of interest is advantageously in the form of plasmid DNA or a viral vector (which vector is derived from an adenovirus, retrovirus, poxvirus, in particular from a vaccinia virus or an MVA virus, herpes virus, adenovirus-associated virus, etc.). The nucleic acid of interest is transported by means of an infectious viral particle or in the form of a synthetic vector (cationic lipid, liposome, cationic polymer, etc.) or an engineered cell (cell which is transfected or transduced with the said nucleic acid) or non-engineered cell (which naturally contains the said nucleic acid).

As regards the variant according to which the nucleic acid is in plasmid DNA form, it is pointed out that the DNA is preferably in solution in water or any aqueous buffer and has not been subjected to precipitation with calcium phosphate prior to its dissolution. The choice of plasmids which can be used within the context of the present invention is vast. They can be of any origin whatsoever (prokaryotic or eukaryotic) or be formed by assembling various elements. In a general way, the plasmids are known to the skilled person. While a large number of them are available commercially, it is also possible to construct them using genetic manipulation techniques (Maniatis et al., 1989, Laboratory Manual, Cold Spring Harbor Laboratory Press, Cold Spring Harbor, N.Y.). The plasmid can be a cloning or expression vector which is derived, for example, from pBR322 (Gibco BRL), pUC (Gibco BRL), pBluescript (Stratagene), pREP4, pCEP4 (Invitrogen) or else p Poly (Lathe et al., Gene, 1987, 57: 193–201). As an indication, the plasmid DNA which is used in the present invention can be amplified and purified in accordance with the general practices of the art. Given that this is a technology which is now widely known, only a brief description will be given of the manner of proceeding, which consists in introducing the plasmid into producer cells (for example *Escherichia coli*), culturing these cells under appropriate conditions (easily established by the skilled person on the basis of his general knowledge in this field and of the selection system carried by the plasmid) and recovering the plasmid DNA using the customary techniques (see, for example, Maniatis et al., 1989, loc. cit.). A purification step can also be envisaged, for example by carrying out the method described in French application FR96 11075, or any other method which is published in the literature.

According to an additionally preferred variant, the nucleic acid of interest is carried by an adenoviral vector which is defective for replication (unable to replicate autonomously in a host cell). The technology of adenoviruses is described in the state of the art (see, for example, Graham and Prevec in Methods in Molecular Biology, 1991, vol 7, pp. 109–128, ed E. J. Murey, The Human Press Inc). Advantageously, the adenoviral vector which is used within the context of the present invention is derived from the genome of an adenovirus, comprises at least the ITRs (inverted terminal repeats) and an encapsidation sequence and lacks all or part of the E1 adenoviral region. In addition, it can lack all or part of the E3 adenoviral region. However, according to an advantageous embodiment, preference is given to retaining the part of the E3 region which encodes polypeptides, in particular the glycoprotein gp19 k (Gooding et al., Critical Review of Immunology, 1990, 10: 53–71), which make it possible to escape the immune system of the host. Furthermore, the vector can contain additional deletions or mutations which affect, in particular, all or part of one or more regions selected from the E2, E4, L1, L2, L3, L4 and L5 regions (see, for example, international application WO 94/28152). In order to illustrate this point, mention may be made of the temperature-sensitive mutation which affects the DBP (standing for DNA-binding protein) gene of the E2 A region (Ensinger et al., J. Virol., 1972, 10: 328–339). Another variant, or attractive combination, consists in deleting the E4 region with the exception of the sequences which encode open reading frames (ORFs) 6 and 7 (these limited deletions do not require the E4 function to be complemented; Ketner et al., Nucleic Acids Res., 1989, 17: 3037–3048). Preferably, the gene(s) of interest is/are inserted into the vector in place of the deleted adenoviral regions, in particular the E1 region. When several genes of interest are used, they can be inserted at the same site or at different sites in the viral genome and can be under the control of the same regulatory elements or of independent elements and, where appropriate, some of them can be in the opposite orientation to the others in order to minimize the phenomena of interference at the level of their expression. The genome of the recombinant adenoviral vector can be prepared by molecular biology techniques or by homologous recombination (see WO 96/17070).

The adenoviral vectors which are used within the context of the present invention are propagated in a complementing cell line which is able to supply the defective function(s) in trans in order to produce the peptides which are required for forming the infectious viral particles. For example, use will be made of cell line 293 for complementing the E1 function (Graham et al., J. Gen. Virol., 1977, 36: 59–72) or of the cell lines described in international application WO 97/04119 for effecting a double complementation. It is also possible to employ an appropriate cell line and a helper virus in order to complement all the defective functions. The viral particles which are produced are recovered from the cell culture and, if need be, purified using the techniques of the art (cesium chloride gradient, chromatographic steps, etc.).

The adenoviral vector which is used within the context of the present invention can be derived from the genome of an adenovirus of human, canine, avian, bovine, murine, ovine, porcine or simian origin or else from a hybrid which comprises adenoviral genome fragments of different origins. Mention may be made, more specifically, of the CAV-1 or CAV-2 adenoviruses of canine origin, of DAV of avian origin, or else of type 3 Bad of bovine origin (Zakharchuk et al., Arch. Virol., 1993, 128: 171–176; Spibey and Cavanagh, J. Gen. Virol., 1989, 70: 165–172; Jouvenne et al., Gene, 1987, 60: 21–28; Mittal et al., J. Gen. Virol., 1995, 76: 93–102). However, preference will be given to an adenoviral vector of human origin which is preferably derived from a serotype C adenovirus, in particular a type 2 or type 5 adenovirus.

The nucleic acid of interest can encode an antisense RNA and/or an mRNA which will then be translated into a polypeptide of therapeutic interest. The nucleic acid can be of the genomic, complementary DNA (cDNA) or mixed (minigene from which at least one intron has been deleted) type, and can be homologous or heterologous in relation to the host cell. The polypeptide which it encodes can correspond to all or part of a protein as is found in nature (native or truncated protein) or a mutant which exhibits improved and/or modified biological properties. The polypeptide can also be a chimeric polypeptide which is the result of fusing sequences of varied origin. The nucleic acid of interest can be obtained by chemical synthesis or by cloning (screening DNA libraries using suitable probes, PCR, etc.) and can be modified using the conventional techniques of molecular biology.

It can be advantageous, within the context of the present invention, to use a gene of interest which encodes a cytokine or a lymphokine (a, b or g interferon, interleukin (IL), in particular IL-2, IL-6, IL-10 or IL-12, a tumor necrosis factor (TNF), a colony stimulating factor (GM-CSF, C-CSF, M-CSF, etc.), a cell or nuclear receptor (in particular those recognized by the HIV virus), a receptor ligand, a protein which is involved in a genetic disease (factor VII, factor VIII, factor IX, dystrophin, insulin, CFTR (cystic fibrosis transmembrane conductance regulator) protein, growth hormone etc.), an enzyme (urease, renin, thrombin, etc.), an enzyme inhibitor (a1-antitrypsin, antithrombin III, viral protease inhibitors, etc.), a polypeptide which has an antineoplastic effect and which is able to at least partially inhibit the initiation or progress of tumors or cancers (antisense RNA, antibody, inhibitor acting at the level of cell division or transduction signals, expression product of a tumor-suppressing gene, for example p53 or Rb, protein which stimulates the immune system, antigen which is associated with a tumor, in particular MUC-1 and E6, E7, L1 and L2 of a papilloma virus, HPV, etc.), a class I or class II antigen of the major histocompatability complex or a polypeptide which acts on the expression of the corresponding genes, a polypeptide which is capable of inhibiting a viral, bacterial or parasitic infection or its development (immunoprotective polypeptide, antigen epitope, antibody, trans-dominant variant, etc.), a cytotoxic product (herpes simplex virus 1 thymidine kinase (HSV-1 TK), ricin, cholera toxin, diphtheria toxin, etc.), an immunotoxin, or a marker polypeptide (b-galactosidase, luciferase, etc.). It should be pointed out that this list is not limiting and that other genes can also be employed.

Furthermore, the nucleic acid of interest which is used in the present invention can also comprise a selection gene which makes it possible to select or identify the transfected cells. Genes which may be mentioned are the neo gene (encoding neomycin phosphotransferase), which confers resistance to the antibiotic G418, the dhfr (dihydrofolate reductase) gene, the CAT (chloramphenicol acetyl transferase) gene, the pac (puromycin acetyl transferase) gene or the gpt (xanthine guanine phosphoribosyl transferase) gene. In a general manner, the selection genes are known to the skilled person.

The gene(s) which is/are carried by the nucleic acid of interest are placed under the control of the elements which are required for expressing them in the cell or host organism. These elements are elements which enable the genes to be transcribed into RNA and an mRNA to be translated into polypeptide. Of these elements, the promoter is of particular importance. It can be isolated from any gene of eukaryotic or even viral origin and can be constitutive or regulatable. Alternatively, the promoter can be the natural promoter of the gene in question. Moreover, the promoter can be modified so as to improve its promoter activity, to suppress a region which inhibits transcription, to render a constitutive promoter regulatable or vice versa, to introduce a restriction site, etc. Mention may be made, by way of example, of the following viral promoters: the CMV (cytomegalovirus) promoter, the RSV (*Rous sarcoma* virus) promoter, the promoter of the HSV1 virus TK gene, the SV40 (simian virus 40) early promoter and the adenoviral MLP (major late promoter) promoter, or of the eukaryotic promoters of the murine or human PGK (phosphoglycerate kinase), a1-antitrypsin (liver-specific), immunoglobulin (lymphocyte-specific), surfactant, CFTR (lung-specific) or actin (muscle-specific) genes. Naturally, the nucleic acid of interest can furthermore comprise additional elements which improve expression (intron sequence, signal sequence, nuclear localization sequence, transcription termination sequence, translation initiation site of the IRES or other type, etc.) or else the maintenance of the nucleic acid in the host cell (origin of replication, etc.). Such elements are known to the skilled person.

As has previously been pointed out, the nucleic acid of interest and the substance leading to disorganization of the extracellular matrix, as comprised in the combination product according to the invention, can be used simultaneously or consecutively or so as to be staggered over time. Simultaneously refers to a coadministration. In this case, these two essential components can be mixed to form a composition prior to being administered, or can be administered at the same time to the cell or the host organism. It is also possible to administer them consecutively, that is to say one after the other, irrespective of which component of the combination product according to the invention is administered first. Finally, it is possible to use a mode of administration which is staggered over time or is intermittent and which stops and restarts at intervals which may or may not be regular. It is pointed out that the routes and sites of administration of the two components can be different. According to one particularly preferred embodiment, the substance leading to disorganization of the extracellular matrix is administered before the nucleic acid, with the route of administration of the two components preferably being similar (for example intramuscular in the two cases). The time interval between the injections is not critical and can be defined by the skilled person. It is possible to recommend an interval of from 10 min to 72 h, advantageously of from 30 min to 48 h, preferably of from 1 to 24 h and, very preferably, of from 1 to 6 h.

In addition, the combination product according to the invention can also be combined with one or more molecule (s) which is/are intended to improve the nucleic acid administration. The molecules can be molecules which have a protective effect on the nucleic acid (protection with regard to degradation in the cell), which improve its penetration or its expression in the host cell (fusogenic peptide, nuclear localization signal, etc.), which enable one particular cell type to be targeted (ligand or antibody which recognizes a cell surface protein, etc.), or which prolong the therapeutic effect (immunosuppressive agent, etc.). The combination product can also be combined with agents which facilitate transfection (proteins, etc.).

The combination product according to the invention can be prepared with a view to local or parenteral administration or to administration by the digestive route. Routes which may in particular be mentioned are the intragastric, subcutaneous, intracardiac, intravenous, intraperitoneal, intrasynovial, intratumor, intrapulmonary, intranasal and intratracheal routes, and, very particularly, the intramuscular route. The administration can be effected by means of any technique of the art (injection, oral route, aerosol, instillation, etc.), as a single dose or as a dose which is repeated once or several times after a particular time interval. The route of administration can be adjusted to suit the gene of interest to be transferred and the disease to be treated. The formulation can include pharmaceutically acceptable vehicles (excipients, adjuvants, etc.). The substance leading to disorganization of the extracellular matrix and the nucleic acid of interest are preferably dissolved in a buffer which is suitable for pharmaceutical use and which can be hypertonic, hypotonic or isotonic. Various buffers can be envisaged. Those which may be mentioned by way of illustration are a physiological saline solution (0.9% NaCl), a nonphysiological saline solution (1.8% NaCl), a Hepes-Ringer solution, a Lactate-Ringer solution, a buffer which is based on tris-HCl (10 mM tris-HCl, pH 7.5 to 8, 1 mM EDTA; 10 mM tris-HCl, pH 7.5 to 8, 1 mM $MgCl_2$), a phosphate buffer (Krebs phosphate $H_2O$ buffer), a sugar (glucose, sucrose, trehalose, etc.) solution, or simply water.

Advantageously, the combination product according to the invention contains a quantity of substance leading to disorganization of the extracellular matrix which is sufficient for improving the diffusion of the nucleic acid of interest, in particular at, or in the vicinity of, the site of injection. The quantity required varies depending on different parameters, for example the substance selected, the route of administration, the target tissue, the individual to be treated or the extent of the area to be treated. The quantity of hyaluronidase which is suitable can correspond to those quantities which are customarily used when administering agents for diffusing pharmacological molecules. As an indication, the dose to be used is between 1 and $10^4$ international units (IU), advantageously between 1 and $10^3$ IU and preferably between 10 and 500 IU.

Furthermore, the quantity of nucleic acid of interest can be defined in terms of the therapeutic gene and the vector employed. In the variant according to which adenoviral particles are used, these particles are preferably formulated in the form of doses of between $10^4$ and $10^{14}$ pfu (plaque-forming units) advantageously between $10^5$ and $10^{13}$ pfu, preferably between $10^6$ and $10^{12}$ pfu. When the nucleic acid of interest is in the form of a plasmid DNA, the quantities can vary from 0.05 to 100 mg, advantageously from 0.1 to 10 mg.

The present invention also relates to the use, for therapeutic or vaccination purposes, of a combination product according to the invention for preparing a medicament which is intended for treating the human or animal body by means of gene therapy, and to the use of a substance which leads to disorganization of the extracellular matrix for improving the diffusion, transfer and/or expression of a nucleic acid of interest into or in a cell or a host organism. The host organism is advantageously a mammal, preferably man. The host cell can be a primary or tumor cell of hematopoietic (totipotent stem cell, leukocyte, monocyte, lymphocyte, macrophage, etc.), muscular (satellite cell, myocyte, myoblast, etc.), hepatic, epithelial, fibroblast, pulmonary or tracheal origin. According to a first possibility, the medicament or the substance can be administered directly in vivo (for example by intravenous or intramuscular injection, into an accessible tumor, into the airways using an aerosol, etc.). It is also possible to adopt the ex vivo approach, which consists in removing cells from the patient (bone marrow stem cells, peripheral blood lymphocytes, etc.), and in treating them in vitro before readministering them to the patient. The substance which leads to disorganization of the extracellular matrix is preferably a hyaluronidase and, according to a preferred embodiment which has already been mentioned, the hyaluronidase is administered prior to the nucleic acid of interest.

The invention also extends to a method of treatment and/or prevention, according to which a therapeutically effective quantity of a combination product according to the invention is administered to a patient who has need of such a treatment. The diseases which are targeted are, in particular, genetic diseases (hemophilia, cystic fibrosis, diabetes, Duchenne's or Becker's muscular dystrophy, etc.), cancers and tumors (which may be induced by oncogenes or viruses), and viral infections (hepatites B and C, AIDS, herpes, etc.). A combination product which can be administered by the intramuscular or intravenous route and which combines hyaluronidase and a nucleic acid expressing the gene for dystrophin is very particularly suitable for treating Duchenne's muscular dystrophy by gene therapy. Thus, the affected muscles are the center of an invasion by connective tissue (and therefore by extracellar matrix). A treatment with hyaluronidase could increase the possibilities for the nucleic acid of interest to diffuse and penetrate into the muscle fibers which are protected by a compact and dense extracellular matrix. Another preferred application is that of treating cystic fibrosis, where hyaluronidase could, at one and the same time, reduce the mucus and enable the therapeutic nucleic acid to diffuse. In this case, it is possible to envisage administering a nucleic acid expressing the CFTR protein into the airways (aerosol, instillation, etc.) or intravenously.

BRIEF DESCRIPTION OF THE DRAWINGS

FIG. 1 demonstrates luciferase transgene levels obtained from lungs or trachea of C57 BL/10 mice following intracheal injections of various doses of hyaluronidase followed three hours later by intratracheal administration of $10^8$ infectious units of a recombinant adenovirus, AdTG8509.

The present invention is illustrated, without, for all that, being limited, by the examples which follow:

EXAMPLE 1

Effect of Hyaluronidase on the Intramuscular Administration of an Adenovirus Encoding the Luciferase Gene The nucleic acid of interest, which contains the luciferase reporter gene placed under the control of the Ad2 MLP promoter and SV40 virus polyadenylation sequences, is carried by an adenoviral vector from which the E1 and E3 regions have been deleted. The final construct, which is designated pTG8509, is prepared using the general techniques of genetic engineering and molecular cloning as detailed in Maniatis et al. (1989, loc. cit.). The first step consists in cloning the luciferase gene expression cassette into a bacterial plasmid. It is possible, for example, to introduce the luciferase gene into the plasmid pTG6580 (described in international application WO 94/28152), which plasmid comprises in a p poly II (Lathe et al., 1987, loc. cit.) structure, the 5' ITR and the encapsidation region of Ad5 (nucleotides 1 to 458 as disclosed in the Genebank database under reference M73260), the Ad2 MLP promoter, a polylinker and the SV40 polyA transcription termination signal (nucleotides 2543 to 2618 as disclosed in the Genebank database under reference J02400), followed by the nucleotides 4047 to 6241 Ad5 sequences. The luciferase cassette is then inserted into the adenoviral skeleton, in place of the E1 region, by means of homologous recombination with the ClaI-linearized vector pTG3602 (see international application WO 96/17070), and into the *E. coli* strain BJ5183 (Hanahan, J. Mol. Biol., 1983, 166: 557–580).

The corresponding adenoviral particles are produced after transfecting the cell line 293 (ATCC CRL1573) with the PacI fragment, which has been isolated from vector pTG8509 and which carries the adenoviral genome; the adenoviral particles are then recovered from the culture after cell lysis (usually 3 consecutive cycles of freezing and thawing). The AdTG8509 adenoviral particles are amplified and purified on a cesium chloride gradient before being administered in vivo.

The combination product tested combines $10^9$ infectious units of AdTG8509 and varying doses of bovine testicular hyaluronidase, which were obtained by diluting a lyophilized preparation (3100 IU Sigma type VI-S) in 0.9% NaCl.

Ten 7-week-old female balb/c mice are divided randomly into 5 experimental groups which are given 25 ml of a solution of hyaluronidase, the doses of which are graded 0 IU, 0.05 IU, 0.1 IU, 1 IU and 10 IU, into the two tibialis anterior muscles followed, 3 hours later, by 25 ml of an AdTG8509 viral suspension having a titer of $10^9$ infectious units. The transfer of the luciferase gene is assessed, after each treated muscle has been excised, one week after the hyaluronidase and the vector were injected. The animals are sacrificed by cervical dislocation and the muscles are immediately removed, frozen in liquid nitrogen and stored at –80° C. The luciferase activity is measured in a luminometer (Microlumat LB 96P, from Berthold) after grinding up the whole muscle and extracting the enzyme (Promega kit). This enzymic activity is manifested in the emission of photons, as expressed in light units per minute (RLU). The administration of hyaluronidase at doses greater than 1 IU is accompanied by a significant increase in the expression of the luciferase gene as compared with the control group (0 IU). The amplification factor is approximately 2 in the animals which are treated with 1 IU of bovine hyaluronidase prior to injection of the recombinant adenoviruses, and 4 in those animals which were given 10 IU of the enzyme.

The experiment is repeated in 7-week-old female C57 BL/10 mice using higher doses of hyaluronidase. Five groups of 3 animals are assembled; the animals are then treated with varying doses of bovine hyaluronidase, with the injection volume being fixed at 25 ml, followed, 3 hours later, by $10^9$ infectious units of AdTG8509 adenovirus (25 ml). The five groups of animals are respectively given 0, 1, 10, 25 and 50 IU of hyaluronidase which is diluted in 0.9% NaCl. As in the previous case, the enzyme and the virus are injected consecutively into the two tibialis anterior muscles of the mice. All the C57 BL/10 mice which have been treated with hyaluronidase express higher levels of luciferase as compared with the control group (0 IU). An amplification factor of approximately 10 is obtained for the product which combines the recombinant adenoviruses and 10 IU of hyaluronidase.

EXAMPLE 2

Effect of Hyaluronidase on the Intracheal Administration of an Adenovirus Encoding the Luciferasegene The C57 BL/10 mice are injected, by the intratracheal route, with different doses of hyaluronidase (0, 0.1, 1, 10 and 50 IU in 25 μl of PBS buffer, given by injection) three hours before $10^8$ IU of AdTG8509, which are distributed in 25 μl of PBS buffer, are administered intratracheally by injection.

The luciferase activity in the trachea and the lungs is determined in the same manner as in Example 1, two days after the adenoviral vector has been administered.

The results are presented in FIG. 1. These results show that the luciferase activity is clearly increased in the presence of the hyaluronidase, both in the lungs and in the trachea. An effect which is linked to the dose of hyaluronidase is clearly seen in the case of expression in the trachea.

The results which are observed appear to indicate that expression of the luciferase gene is weaker in the lungs than in the trachea. This unexpected result could be explained by a bronchoconstriction or obstruction reaction taking place in the lungs with these reactions being linked to the first administration of hyaluronidase to an animal of small size.

These results nevertheless show that pretreatment with hyaluronidase makes it possible to improve the efficacy of the expression, in the airways, of the genes which are carried by the adenovirus which is subsequently administered. The use of an aerosol as the means of administration should make it possible to limit the negative effect of repeated intratracheal administrations in the mouse on account of the more reduced volume of the compositions which are administered.

What is claimed is:

1. A composition comprising at least a nucleic acid and at least one substance which disorganizes the extracellular matrix of a cell, said substance being a hyaluronidase, wherein said nucleic acid is contained in an infectious viral particle, a cationic lipid, a liposome or a cationic polymer.

2. The composition according to claim 1, wherein said hyaluronidase is a mammalian, reptilian or hymenopteran hyaluronate glycanohydrolase, a hyaluronate glycanohydrolase from the salivary gland of a leech, or a bacterial hyaluronate lyase.

3. The composition according to claim 1, wherein the nucleic acid is in the form of a recombinant adenoviral vector which is defective for replication.

4. The composition according to claim 3, wherein the adenoviral vector comprises at least ITRs and an encapsidation sequence and lacks all or part of adenoviral E1 region.

5. The composition according to claim 4, wherein the adenoviral vector additionally lacks all or part of the adenoviral E3 region.

6. The composition according to claim 4, wherein the adenoviral vector additionally lacks all or part of one or more regions selected from the adervirol E2, E4, L1, L2, L3, L4 and L5 regions.

7. The composition according to claim 1, which further comprises a pharmaceutically acceptable excipient.

8. A method for enhancing delivery of a nucleic acid into a human or an animal, said method comprising the step of administering hyaluronidase to the human or the animal prior to or in conjunction with an infectious viral particle or a complex comprising a nucleic acid and a cationic lipid, a liposome or a cationic polymer.

9. The method of claim 8, wherein said infectious viral particle or said complex comprising a nucleic acid and a cationic lipid, a liposome or a cationic polymer is administered simultaneously with said hyaluronidase.

10. The method of claim 8, wherein said infectious viral particle or said complex comprising a nucleic acid and a cationic lipid, a liposome or a cationic polymer is administered following the administration of hyaluronidase.

11. The method of claim 9, wherein said infectious particle is an adenoviral particle.

12. The method of claim 10, wherein said infectious viral particle is an adenoviral particle.

13. A kit for enhancing introduction of a nucleic acid into a cell comprising (i) at least a hyaluronidase and (ii) at least one nucleic acid wherein said nucleic acid is contained in an infectious viral particle, a cationic lipid, a liposome or a cationic polymer.

* * * * *

UNITED STATES PATENT AND TRADEMARK OFFICE
CERTIFICATE OF CORRECTION

PATENT NO.   : 6,258,791 B1
DATED        : July 10, 2001
INVENTOR(S)  : Serge Braun It is certified that error appears in the above-identified patent and that said Letters Patent is hereby corrected as shown below:

<u>Title page,</u>
Item [73], Assignee, please insert -- and Association Francaise Contre Les Myopathies, Paris (FR) --

This certificate supersedes Certificate of Correction issued May 14, 2002

Signed and Sealed this

Twenty-third Day of July, 2002

*Attest:*

*Attesting Officer*

JAMES E. ROGAN
*Director of the United States Patent and Trademark Office*